United States Patent
Clark et al.

(10) Patent No.: US 10,238,568 B2
(45) Date of Patent: Mar. 26, 2019

(54) RELEASE HANDLE MECHANISMS FOR A SPAR OF A LIMB HOLDER

(71) Applicant: Allen Medical Systems, Inc., Batesville, IN (US)

(72) Inventors: Andrew D. Clark, Allston, MA (US); Jesse S. Drake, Westborough, MA (US); Anthony V. Catacchio, Arlington, MA (US); Dustin T. Libby, Naples, FL (US); Mark A. Sutherland, Sterling, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 365 days.

(21) Appl. No.: 14/869,339

(22) Filed: Sep. 29, 2015

(65) Prior Publication Data

US 2016/0051432 A1 Feb. 25, 2016

Related U.S. Application Data

(63) Continuation of application No. 13/790,148, filed on Mar. 8, 2013, now Pat. No. 9,161,875.
(Continued)

(51) Int. Cl.
*A61G 13/12* (2006.01)
*A61F 5/04* (2006.01)
(Continued)

(52) U.S. Cl.
CPC ............ *A61G 13/1205* (2013.01); *A61F 5/04* (2013.01); *A61G 13/0036* (2013.01);
(Continued)

(58) Field of Classification Search
CPC ............ A61G 13/0036; A61G 13/0063; A61G 13/0081; A61G 13/101; A61G 13/12;
(Continued)

(56) References Cited

U.S. PATENT DOCUMENTS

| 870,324 A | 11/1907 | Thorner |
| 2,188,592 A | 1/1940 | Cunningham |

(Continued)

FOREIGN PATENT DOCUMENTS

| WO | 2001093796 A2 | 12/2001 |
| WO | 2005020819 | 3/2005 |

(Continued)

OTHER PUBLICATIONS

International Search Report for PCT International Application Serial No. PCT/US2008/074028, completed Nov. 7, 2008, (6 pages).
(Continued)

*Primary Examiner* — Nicholas F Polito
(74) *Attorney, Agent, or Firm* — Barnes & Thornburg LLP

(57) ABSTRACT

A patient support apparatus includes a surgical table and a limb support unit coupled to the surgical table. The limb support unit includes a support platform coupled to the surgical table in a fixed position, a first limb holder coupled to the support platform in a fixed position relative to the support platform, and a second limb holder coupled to the support platform and spaced apart from the first limb holder. The first limb holder includes a multi-axis joint coupled to the support platform in a fixed position and a spar coupled to the multi-axis joint to move relative to the support platform while supporting a patient's limb that has been coupled to the spar.

21 Claims, 13 Drawing Sheets

Related U.S. Application Data

(60) Provisional application No. 61/698,157, filed on Sep. 7, 2012.

(51) Int. Cl.
*A61G 13/00* (2006.01)
*A61G 13/10* (2006.01)

(52) U.S. Cl.
CPC ......... *A61G 13/101* (2013.01); *A61G 13/125* (2013.01); *A61G 13/1245* (2013.01); *A61G 13/1285* (2013.01)

(58) Field of Classification Search
CPC .............. A61G 13/1205; A61G 13/123; A61G 13/1245; A61G 13/125; A61G 13/1285; A61F 5/04
See application file for complete search history.

(56) References Cited

U.S. PATENT DOCUMENTS

| | | |
|---|---|---|
| 2,509,086 A | 5/1950 | Eaton |
| 2,872,259 A | 2/1959 | Thorpe |
| 2,935,286 A | 5/1960 | Parsons |
| 3,015,113 A | 1/1962 | Wallen |
| 3,042,025 A | 7/1962 | Jackson |
| 3,046,072 A | 7/1962 | Douglass, Jr. et al. |
| 3,099,441 A | 7/1963 | Ries |
| 3,188,079 A | 6/1965 | Boetcker et al. |
| 3,828,377 A | 8/1974 | Fary, Sr. |
| 3,873,081 A | 3/1975 | Smith |
| 3,946,452 A | 3/1976 | Eary, Sr. |
| 3,947,686 A | 3/1976 | Cooper et al. |
| 4,018,412 A | 4/1977 | Kees, Jr. et al. |
| 4,028,754 A | 6/1977 | Eary, Sr. |
| 4,033,339 A | 7/1977 | Roberts et al. |
| 4,054,282 A | 10/1977 | Hamer |
| 4,108,426 A | 8/1978 | Lindstroem et al. |
| 4,139,917 A | 2/1979 | Fenwick |
| 4,143,652 A | 3/1979 | Meier et al. |
| 4,225,125 A | 9/1980 | Lee |
| 4,239,200 A | 12/1980 | Sarrafian et al. |
| 4,346,488 A | 8/1982 | Eary, Sr. |
| 4,355,631 A | 10/1982 | LeVahn |
| 4,383,351 A | 5/1983 | Fenwick |
| 4,391,438 A | 7/1983 | Heffington, Jr. |
| 4,398,707 A | 8/1983 | Cloward |
| D271,834 S | 12/1983 | Huntsinger |
| 4,455,698 A | 6/1984 | Eary, Sr. |
| 4,474,364 A | 10/1984 | Brendgord |
| 4,487,523 A | 12/1984 | Monroe |
| 4,506,872 A | 3/1985 | Westerberg |
| 4,520,800 A | 6/1985 | Kowalski |
| 4,526,355 A | 7/1985 | Moore et al. |
| 4,527,555 A | 7/1985 | Ruf |
| 4,527,787 A | 7/1985 | Collis, Jr. |
| 4,531,247 A | 7/1985 | Eary, Sr. |
| 4,549,501 A | 10/1985 | Anderson et al. |
| 4,558,857 A | 12/1985 | Heller |
| 4,559,930 A | 12/1985 | Cobiski |
| 4,562,588 A | 12/1985 | Ruf |
| 4,583,725 A | 4/1986 | Arnold |
| 4,616,813 A | 10/1986 | McConnell |
| 4,635,914 A | 1/1987 | Kabanek |
| 4,653,482 A | 3/1987 | Kurland |
| 4,662,619 A | 5/1987 | Ray et al. |
| 4,671,728 A | 6/1987 | Clark et al. |
| 4,712,781 A | 12/1987 | Watanabe |
| 4,729,535 A | 3/1988 | Frazier et al. |
| 4,752,064 A | 6/1988 | Voss |
| 4,796,846 A | 1/1989 | Heier et al. |
| 4,827,541 A | 5/1989 | Breme et al. |
| 4,840,363 A | 6/1989 | McConnell |
| 4,852,840 A | 8/1989 | Marks |
| 4,866,796 A | 9/1989 | Robinson et al. |
| 4,872,656 A | 10/1989 | Brendgord et al. |
| 4,901,963 A | 2/1990 | Yoder |
| 4,901,964 A | 2/1990 | McConnell |
| 4,908,892 A | 3/1990 | Michelson |
| 4,971,037 A | 11/1990 | Pelta |
| 4,989,848 A | 2/1991 | Monroe |
| 4,995,067 A | 2/1991 | Royster et al. |
| 5,009,407 A | 4/1991 | Watanabe |
| 5,088,706 A | 2/1992 | Jackson |
| 5,108,213 A | 4/1992 | Shields |
| 5,131,106 A | 4/1992 | Jackson |
| 5,121,892 A | 6/1992 | Herzog |
| 5,135,210 A | 8/1992 | Michelson |
| 5,163,193 A | 11/1992 | Whitmore |
| 5,197,975 A | 3/1993 | Mombrine |
| 5,239,716 A | 8/1993 | Fisk |
| 5,276,927 A | 1/1994 | Day |
| 5,279,310 A | 1/1994 | Hsien |
| 5,287,575 A | 2/1994 | Allen et al. |
| 5,297,303 A | 3/1994 | Stafford et al. |
| 5,297,539 A | 3/1994 | Liebl et al. |
| 5,320,444 A | 6/1994 | Bookwalter et al. |
| 5,400,772 A | 3/1995 | LeVahn et al. |
| 5,444,882 A | 8/1995 | Andrews et al. |
| 5,452,728 A | 9/1995 | Iams |
| 5,489,258 A | 2/1996 | Wohnsen et al. |
| 5,520,623 A | 5/1996 | Williams |
| 5,535,466 A | 7/1996 | Snell |
| 5,538,215 A | 7/1996 | Hosey |
| 5,566,682 A | 10/1996 | Yavitz |
| 5,575,027 A | 11/1996 | Mueller |
| 5,613,254 A | 3/1997 | Clayman et al. |
| 5,628,078 A | 5/1997 | Pennington et al. |
| 5,642,302 A | 6/1997 | Dumont et al. |
| 5,645,079 A | 7/1997 | Zahiri et al. |
| 5,655,238 A | 8/1997 | Stickley et al. |
| 5,658,315 A | 8/1997 | Lamb et al. |
| 5,675,851 A | 10/1997 | Feathers |
| 5,680,861 A | 10/1997 | Rohling |
| 5,701,991 A | 12/1997 | Helmetsle |
| 5,741,210 A | 4/1998 | Dobrovolny |
| 5,758,374 A | 6/1998 | Ronci |
| 5,758,647 A | 6/1998 | Cummins |
| 5,836,026 A | 11/1998 | Reed |
| 5,836,559 A | 11/1998 | Ronci |
| 5,926,876 A | 7/1999 | Haigh et al. |
| D414,974 S | 10/1999 | Marrone, II et al. |
| 6,001,076 A | 12/1999 | Wilson et al. |
| 6,003,174 A | 12/1999 | Kantrowitz et al. |
| 6,065,165 A | 5/2000 | Delk et al. |
| 6,076,525 A | 6/2000 | Hoffman |
| 6,154,901 A | 12/2000 | Carr |
| 6,154,903 A | 12/2000 | Wai-Chung |
| 6,195,820 B1 | 3/2001 | Heimbrock et al. |
| 6,199,233 B1 | 3/2001 | Krantrowitz et al. |
| 6,199,552 B1 | 3/2001 | Crespo |
| 6,237,172 B1 | 5/2001 | Morgan, Sr. |
| 6,260,220 B1 | 7/2001 | Lamb et al. |
| 6,295,671 B1 | 10/2001 | Reesby et al. |
| 6,324,710 B1 | 12/2001 | Hernandez et al. |
| 6,336,412 B2 | 1/2002 | Heimbrock et al. |
| 6,382,576 B1 | 5/2002 | Heimbrock |
| 6,385,802 B1 | 5/2002 | Roberts et al. |
| 6,428,497 B1 | 8/2002 | Crouch |
| 6,526,609 B2 | 3/2003 | Wong |
| 6,557,195 B2 | 5/2003 | Dinkler |
| 6,584,630 B1 | 7/2003 | Dinkler |
| 6,622,324 B2 | 9/2003 | Vansteenburg |
| 6,622,980 B2 | 9/2003 | Boucher et al. |
| 6,663,055 B2 | 12/2003 | Boucher et al. |
| 6,691,350 B2 | 2/2004 | Weismiller |
| 6,701,553 B1 | 3/2004 | Hand et al. |
| 6,718,581 B2 | 4/2004 | Riach |
| 6,754,923 B2 | 6/2004 | Borders et al. |
| 6,813,788 B2 | 11/2004 | Dinkler et al. |
| 7,017,211 B2 | 3/2006 | Krywiczanin et al. |
| 7,020,917 B1 | 4/2006 | Kolody et al. |
| 7,520,007 B2 | 4/2009 | Skripps |
| 7,520,008 B2 | 4/2009 | Wong et al. |

(56) References Cited

U.S. PATENT DOCUMENTS

| | | |
|---|---|---|
| 7,600,281 B2 | 10/2009 | Skripps |
| 7,669,262 B2 | 3/2010 | Skripps et al. |
| 8,683,631 B2 * | 4/2014 | Bellows ............ A61G 13/0036 128/845 |
| 9,161,875 B2 | 10/2015 | Clark et al. |
| 2002/0032927 A1 | 3/2002 | Dinkler |
| 2002/0061225 A1 | 5/2002 | Boucher et al. |
| 2002/0061255 A1 | 5/2002 | Nguyen et al. |
| 2002/0170115 A1 | 11/2002 | Borders et al. |
| 2003/0028967 A1 | 2/2003 | Schuerch |
| 2003/0061660 A1 | 4/2003 | Easterling |
| 2003/0167569 A1 | 9/2003 | Newkirk et al. |
| 2004/0123389 A1 | 7/2004 | Boucher et al. |
| 2004/0133979 A1 | 7/2004 | Newkirk et al. |
| 2004/0133983 A1 | 7/2004 | Newkirk et al. |
| 2005/0160533 A1 | 7/2005 | Boucher et al. |
| 2005/0268400 A1 | 12/2005 | Siccardi et al. |
| 2006/0225743 A1 * | 10/2006 | Schuerch ............... A61G 13/12 128/845 |
| 2006/0253985 A1 | 11/2006 | Skripps |
| 2007/0074347 A1 | 4/2007 | Coppens et al. |
| 2007/0265635 A1 | 11/2007 | Torrie et al. |
| 2008/0078031 A1 | 4/2008 | Weinstein et al. |
| 2011/0023893 A1 * | 2/2011 | Striggow ............... A61G 13/12 128/882 |
| 2013/0081635 A1 | 4/2013 | Drake et al. |
| 2014/0068863 A1 | 3/2014 | Clark et al. |
| 2014/0215718 A1 | 8/2014 | Wootton |

FOREIGN PATENT DOCUMENTS

| | | |
|---|---|---|
| WO | 2005020819 A1 | 3/2005 |
| WO | 2009029524 A1 | 3/2009 |
| WO | 2009062324 A1 | 5/2009 |

OTHER PUBLICATIONS

EP Communication pursuant to Article 94(3) EPC for Application No. 13183032.5-1651, dated Aug. 14, 2015 (4 pages).

EP Search Report for Application No. 13183032.5-1651, dated Sep. 1, 2014 (6 pages).

* cited by examiner

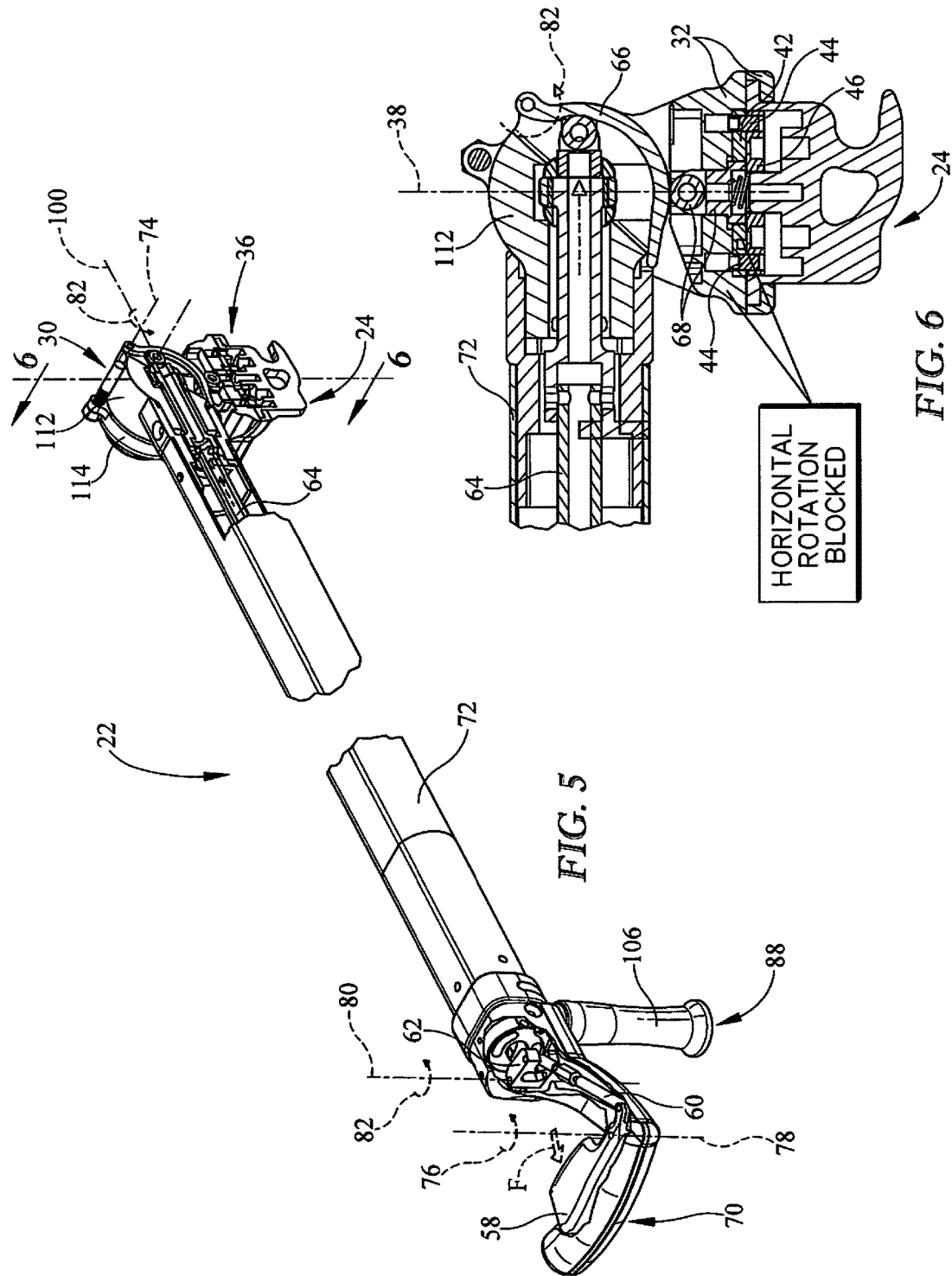

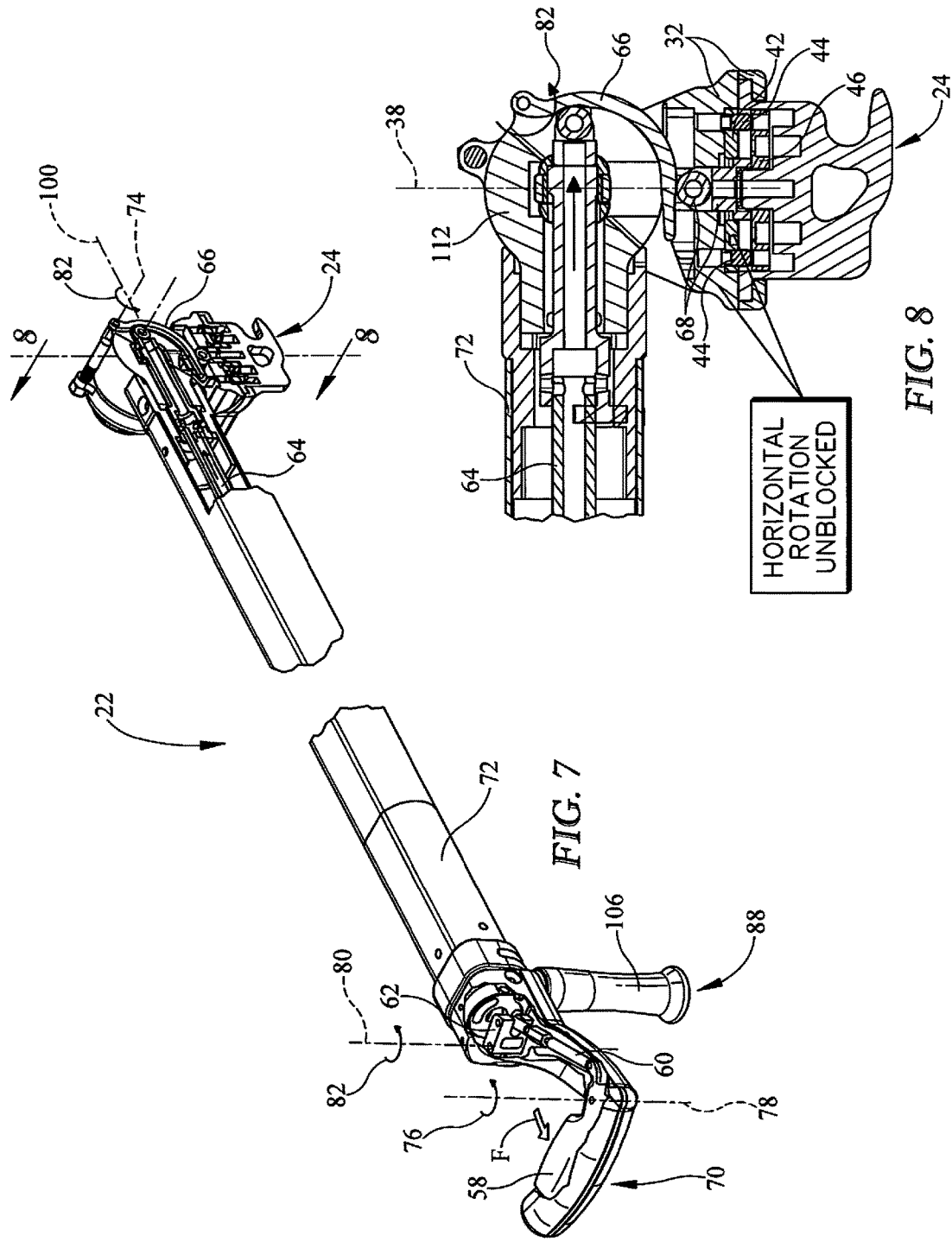

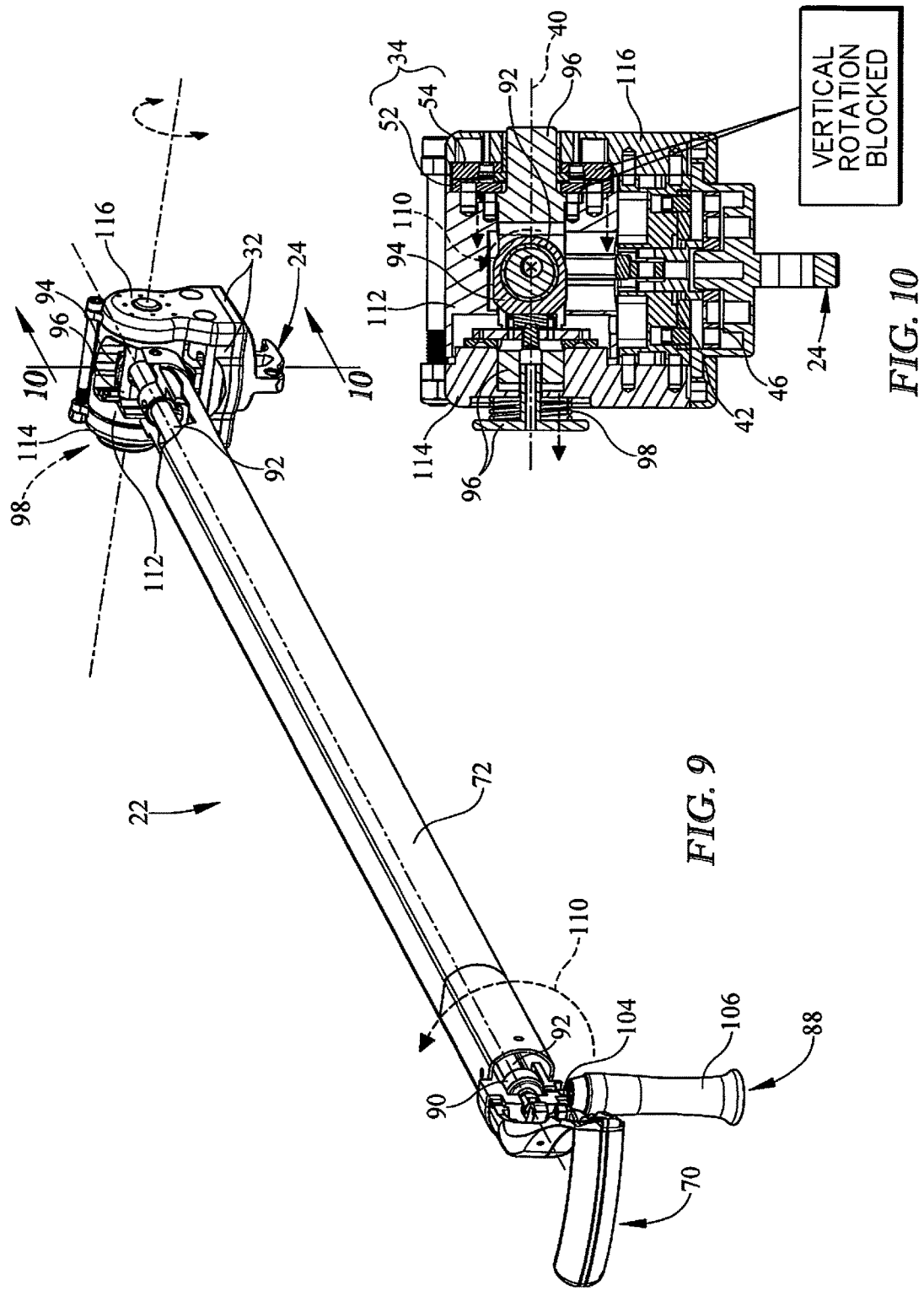

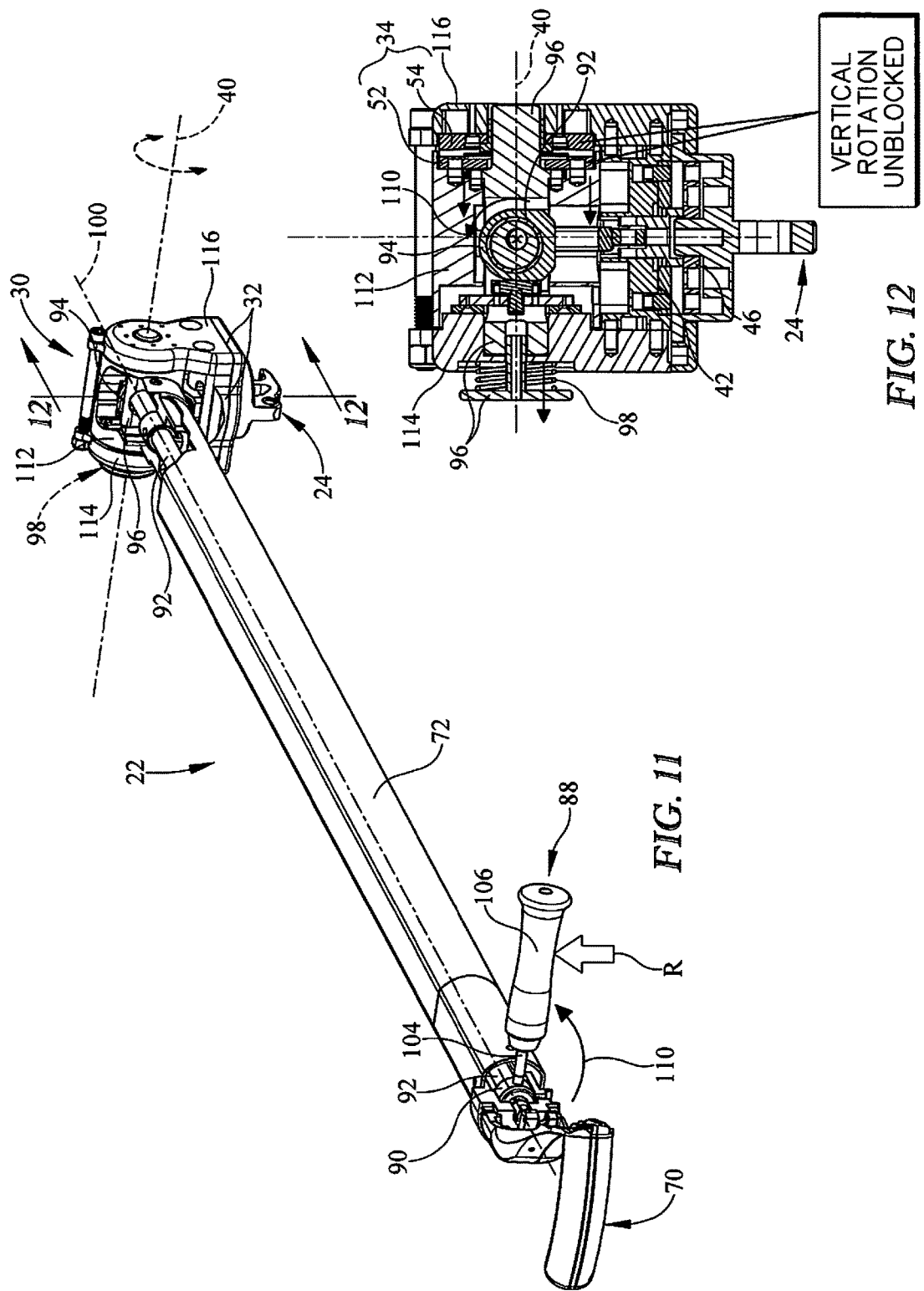

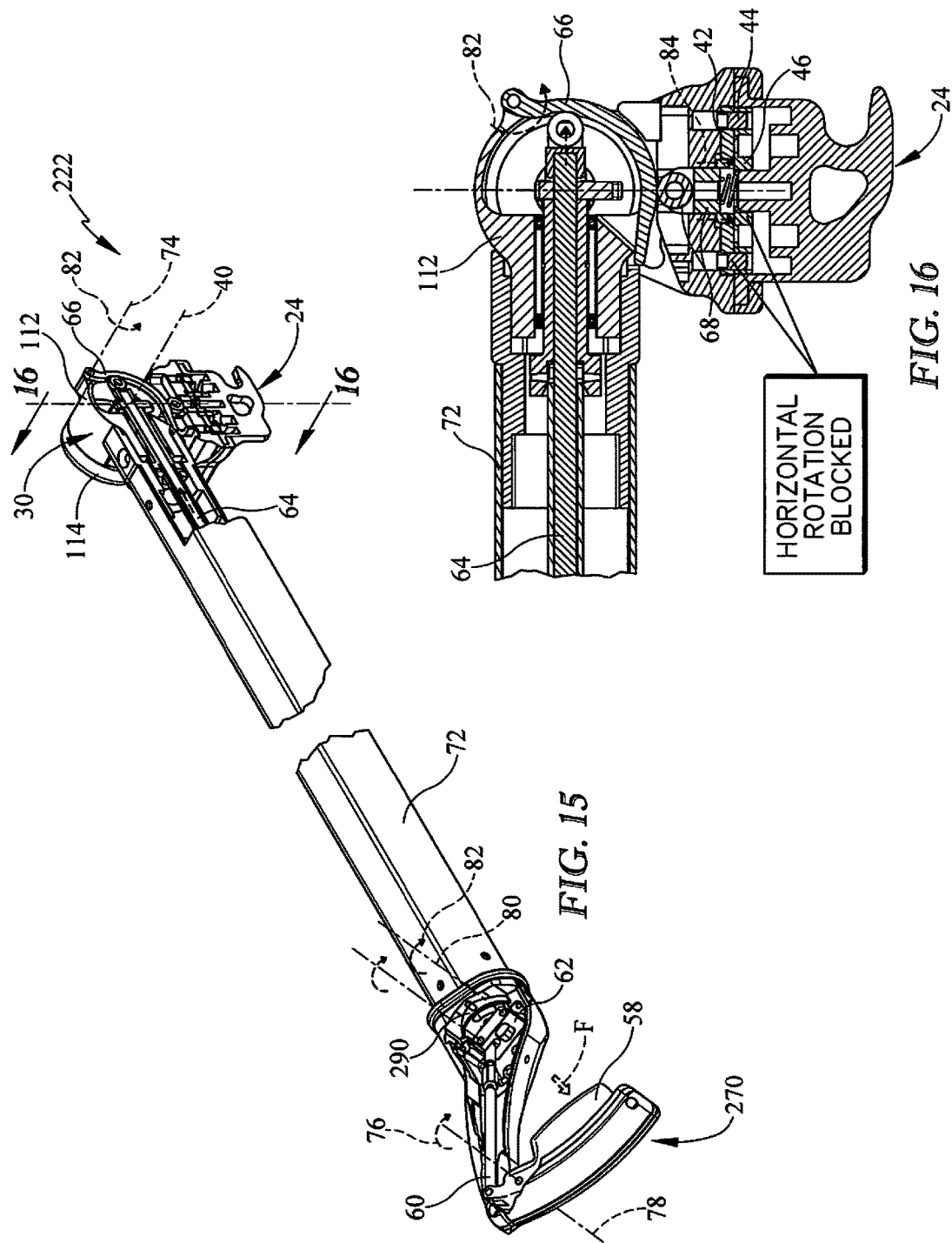

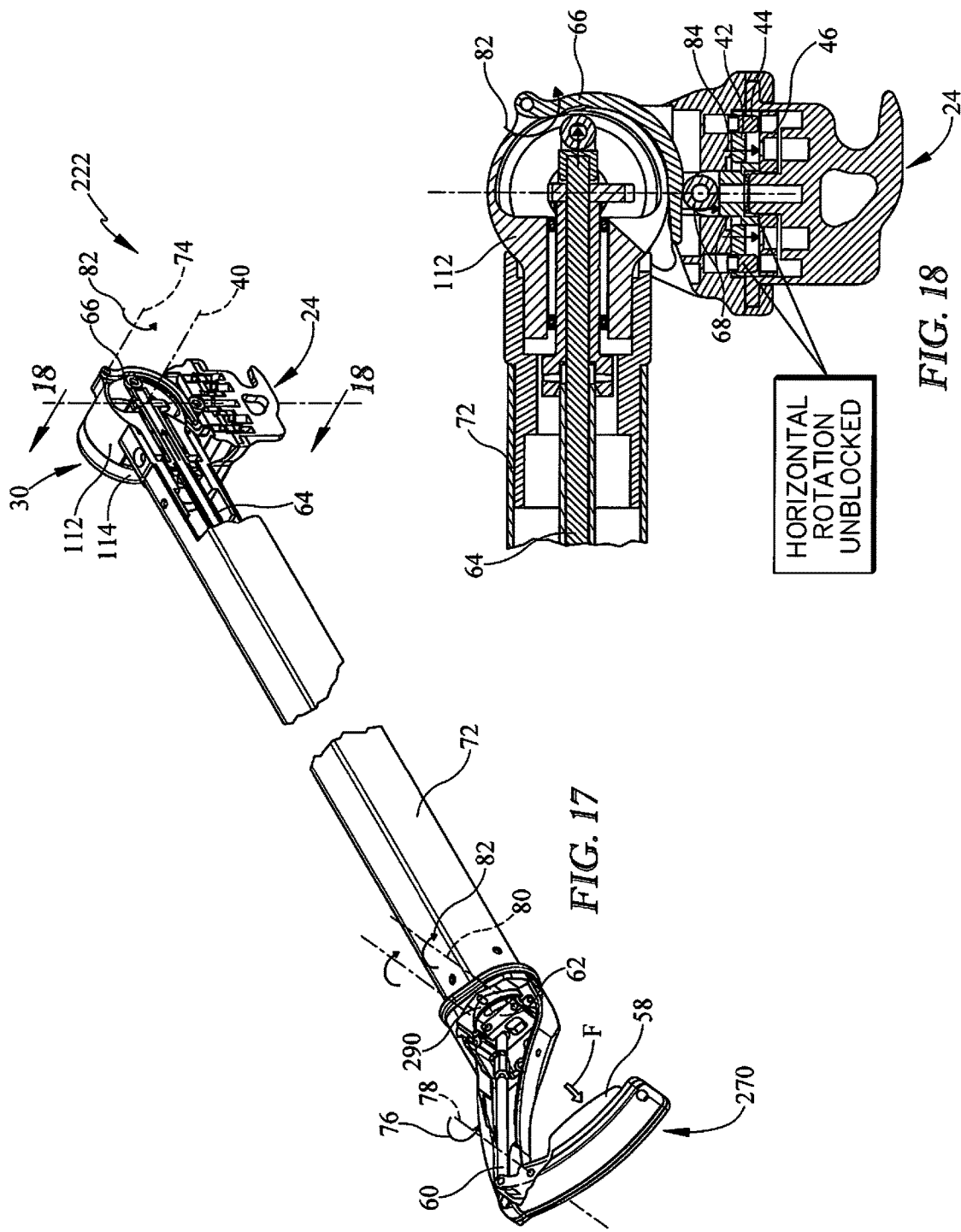

RELEASE HANDLE MECHANISMS FOR A SPAR OF A LIMB HOLDER

PRIORITY CLAIM

This application is a continuation of U.S. application Ser. No. 13/790,148, filed Mar. 8, 2013, which claims priority under 35 U.S.C. § 119(e) to U.S. Provisional Application Ser. No. 61/698,157, filed Sep. 7, 2012, each of which is expressly incorporated by reference herein

BACKGROUND

The present disclosure is related to a support apparatus for supporting a patient. More particularly, the present disclosure relates to a support apparatus including a surgical table and a limb support coupled to the surgical table.

Support apparatuses include a surgical table and a limb support. The limb support includes a support platform coupled to one end of the surgical table, a first limb holder, and a second limb holder. Each limb holder is coupled to the support platform and configured to support a patient's limb during surgery. The patient's limb may be placed in tension to aid the surgeon performing the surgery. The limb holder may be arranged in any number of positions relative to the support platform during surgery on the patient while the patient's limb is in tension.

A limb holder may move in unintended ways during movement of the patient's limb during surgery while the patient's limb is maintained in tension. Unintended movement of the patient's limb may be minimized by moving the two-axis limb holder in only one plane of movement at a time. As a result, movement of the limb holder should be performed in only one plane of movement at a time so that tension is not lost on the patient's limb.

SUMMARY

The present application discloses one or more of the features recited in the appended claims and/or the following features which, alone or in any combination, may comprise patentable subject matter.

According to one aspect of the present disclosure, a limb holder includes a joint mount, a spar, and a multi-axis joint. The mount is adapted to couple to a platform in a fixed position. The spar is arranged to extend in an outward direction away from the joint mount and is adapted to couple to a patient's foot and retain the patient's foot in tension during a procedure. The multi-axis joint is arranged to interconnect the spar and the joint mount to cause the spar to move relative to the joint mount.

In some embodiments, the multi-axis joint may include a vertical-position lock and a horizontal-position lock. The horizontal-position lock may interconnect the spar and the vertical-position lock. The horizontal-position lock may be movable between a blocking position in which movement of the spar and the vertical-position lock is blocked and an unblocking position in which the spar and the vertical-position lock are freed to move together relative to the joint mount about a vertical axis. The vertical-position lock may interconnect the spar and the horizontal-position lock. The vertical-position lock may be movable between a locked position in which the spar is blocked from moving relative to the horizontal-position lock and the joint mount and an unlocked position in which the spar is freed to move relative to the horizontal-position lock and the joint mount.

In some embodiments, the spar and the vertical-position lock may be freed to move about a vertical axis when the horizontal-position lock is in the unblocking position. The spar may be freed to move about a horizontal axis when the vertical-position lock is in the unlocked position.

In some embodiments, the multi-axis joint may further include a support platform. The horizontal-position lock may lie between and interconnect the joint mount and the support platform to cause the support platform to move relative to the joint mount.

In some embodiments, the multi-axis joint may further include a joint housing coupled to the support platform to move therewith. The vertical-position lock may interconnect portions of the joint housing and the spar to cause the portions of the joint housing and the spar to move relative to the support platform.

In some embodiments, the horizontal-position lock may include a stationary disk, a set of movable pins, and movable disk. The stationary disk may be coupled to the support platform in a fixed position relative to the support platform. The set of movable pins may be coupled to the support platform and biased to extend away from the support platform toward the joint mount. The movable disk may be coupled to the joint mount to move relative to the joint mount, the stationary disk, and the set of movable pins when the horizontal-position lock is in the unblocking position.

In some embodiments, the stationary disk may be formed to include a set of stationary-disk holes having a first quantity. The movable disk may be formed to include a set of movable-disk holes having a second quantity. The set of movable pins may have a third quantity. At least two pins included in the set of movable pins may extend through two stationary-disk holes and two movable-disk holes when the horizontal-position lock is in the blocking position.

In some embodiments, the movable disk may be spaced apart from the stationary disk. As a result, the set of movable pins may be disengaged from the movable disk so that none of the movable pins extend through any of the movable-disk holes when the horizontal-position lock is in the unblocking position. In some embodiments, the first quantity may be equal to the second quantity and the third quantity is less than the first quantity. The horizontal-position lock may be movable in about 4.5 degree increments.

In some embodiments, each movable pin included in the set of movable pins may be spaced-apart circumferentially an equal distance from each neighboring movable pin. Each stationary-disk hole may be spaced-apart circumferentially an equal distance from each neighboring stationary-disk hole. Each movable-disk hole may be spaced-apart circumferentially an equal amount from each neighboring movable-disk hole.

In some embodiments, the horizontal-position lock may be movable in about 4.5 degree increments. The vertical-position lock may be movable in about 4 degree increments.

In some embodiments, the joint housing may include a first shell support, a second shell support, and a housing shell. The first shell support may be coupled to the support platform to move therewith. The second shell may be coupled to the support platform in spaced-apart relation to move therewith. The housing shell may be coupled to the spar to move therewith and to the first and second shell supports to move relative to the first and second shell supports.

In some embodiments, the vertical-position lock may include a stationary plate and a movable plate. The stationary plate may be coupled to the second shell support to move therewith. The movable plate may be coupled to the housing shell to move therewith and relative to the stationary plate.

In some embodiments, the movable plate may engage the stationary plate when the vertical-position lock is in the locked position. The movable plate may be spaced apart from and disengaging the stationary plate when the vertical-position lock is in the unlocked position.

In some embodiments, the stationary plate may include a disk and a plurality of radially-extending teeth appended to the disk. The plurality of radially-extending teeth may be arranged to extend toward the movable plate. The plurality of teeth may be spaced-apart equally from one another.

In some embodiments, the movable plate may include a disk and a plurality of radially-extending teeth appended to the disk. The plurality radially-extending teeth may be arranged to extend toward the stationary plate. The plurality of radially-extending teeth may be spaced-apart equally from one another.

In some embodiments, the vertical-position lock may be movable in about 4 degree increments. The horizontal-lock actuator may be coupled to the horizontal-position lock to cause the horizontal-position lock to move between the blocking and unblocking positions.

In some embodiments, the horizontal-lock actuator may include a trigger, a linkage, a lever, and a drive linkage. The trigger may be coupled to the spar to move relative to the spar in response to application of an actuation force to the trigger. The linkage may be coupled to the trigger to move therewith. The lever may be coupled to the linkage to move therewith about a pivot axis. The drive linkage may be coupled to a movable disk included in the horizontal-position lock.

In some embodiments, application of the actuation force may cause the lever to engage and move the drive linkage which causes the movable disk of the horizontal-position lock to move away from and out of engagement with a set of movable pins included in the horizontal-position lock. As a result, the horizontal-position lock may assume the unblocking position.

In some embodiments, the spar and the vertical-position lock may be freed to move about a vertical axis when the horizontal-position lock is in the unblocking position. The spar may be freed to move about a horizontal axis when the vertical-position lock is in the unlocked position. The pivot axis may be spaced apart from and generally parallel to the horizontal axis.

In some embodiments, the horizontal-lock actuator may further include a horizontal-lock bias spring. The horizontal-lock bias spring may be positioned to lie between the joint mount and the drive linkage. The horizontal-lock actuator may be configured to provide a bias force to the horizontal-position lock to cause the horizontal-position lock to assume the blocking position when the actuation force is removed from the trigger. The vertical-lock actuator may be coupled to the vertical-position lock to cause the vertical-position lock to move between the locked and the unlocked positions.

In some embodiments, the vertical-lock actuator may include a grip, a rotation collar, a cam, and a cam follower. The grip may be coupled to the spar to extend perpendicularly away from the spar and move relative to the spar in response to application of a rotation force to the grip. The rotation collar may be coupled to the grip to move therewith about a rotation axis. The cam may be coupled to the rotation collar to move therewith. The cam follower may be coupled to the vertical-position to lock to cause the vertical-position lock to move between the locked and the unlocked position in response to rotation of the grip about the rotation axis.

In some embodiments, the vertical-lock actuator may further include a rotation linkage. The rotation linkage may be arranged to interconnect the rotation collar and the cam to cause movement of the rotation collar to be translated to the cam.

In some embodiments, the horizontal-lock actuator may include a trigger, a linkage, a lever, and a drive linkage. The trigger may be coupled to the spar to move relative to the spar in response to application of an actuation force to the trigger. The linkage may be coupled to the trigger to move therewith. The lever may be coupled to the linkage to move therewith about a pivot axis. The drive linkage may be coupled to a movable disk included in the horizontal-position lock.

In some embodiments, the rotation linkage may be formed to include a hollow passageway therein. A portion of the linkage may be arranged to extend through the hollow passageway to cause movement of the linkage to be independent of movement of the rotation linkage.

In some embodiments, the multi-axis joint may further include a joint housing coupled to the support platform to move therewith. The vertical-position lock may interconnect portions of the joint housing and the spar to cause the portions of the joint housing and the spar to move relative to the support platform. The joint housing may include a first shell support, a second shell support, and a housing shell. The first shell support may be coupled to the support platform to move therewith. The second shell may be coupled to the support platform in spaced-apart relation to move therewith. The housing shell may be coupled to the spar to move therewith and to the first and second shell supports to move relative to the first and second shell supports. The vertical-position lock may include a stationary plate and a movable plate. The stationary plate may be coupled to the second shell support to move therewith. The movable plate may be coupled to the housing shell and the cam follower to move therewith and relative to the stationary plate. Movement of the grip may cause the cam to move the cam follower causing the cam follower, the housing shell, and the movable plate of the vertical-position lock to move back and forth along a horizontal axis. The spar may be freed to move about the horizontal axis when the vertical-position lock is in the unlocked position.

In some embodiments, the horizontal-lock actuator may further include a bias mechanism. The bias mechanism may be positioned to lie between a portion of the cam follower and the first shell support. The bias mechanism may be configured to bias the cam follower and the movable plate of the vertical-position lock away from the stationary plate of the vertical-position lock.

In some embodiments, the spar may be movable about a horizontal axis through a range of motion. The range of motion may be about 20 degrees down from a generally horizontal position of the spar and about 55 degrees up from the generally horizontal position of the spar.

In some embodiments, the limb holder may be configured to support a leg of a patient. The patient may have a weight of about 350 pounds and an inseam of about 42 inches. The limb holder may withstand a torque of about 250 foot pounds when the spar is in the generally horizontal position.

In some embodiments, the vertical-position lock moves from the blocking position to the unblocking position when the horizontal-position lock is in the locked position. The vertical-position lock may move from the blocking position to the unblocking position when the horizontal-position lock is in the unlocked position. The horizontal-position lock may move from the locked position to the unlocked position when the vertical-position lock is in the blocking position. The horizontal-position lock may move from the locked position to the unlocked position when the vertical-position lock is in the unblocking position.

In some embodiments, the multi-axis joint may further include a support platform and a joint housing. The horizontal-position lock may lie between and interconnect the joint mount and the support platform to cause the support platform to move relative to the joint mount. The joint housing may be coupled to the support platform to move therewith. The vertical-position lock may interconnect portions of the joint housing and the spar to cause the portions of the joint housing and the spar to move relative to the support platform.

In some embodiments, the vertical-position lock may include a vertical stationary disk, a vertical movable disk, and a set movable pins. The stationary disk may be coupled to joint housing in a fixed position relative to the joint housing. The vertical movable disk may be coupled to the joint housing to move relative to the joint housing. The set of movable pins may be trapped between the vertical stationary disk and the vertical movable disk and biased to extend away from the vertical stationary disk toward the vertical movable disk and engage the vertical movable disk when the vertical-position lock is in the locked position.

In some embodiments, the vertical stationary disk may be formed to include a set of stationary-disk holes having a first quantity. The vertical movable disk may be formed to include a set of movable-disk holes having a second quantity. The set of movable pins may have a third quantity, and at least two pins included in the set of movable pins extends through two stationary-disk holes and two movable-disk holes when the vertical-position lock is in the locked position.

In some embodiments, the vertical movable disk may be spaced apart from the vertical stationary disk to cause the set of movable pins to be disengaged from the vertical movable disk. As a result, none of the movable pins may extend through any of the movable-disk holes when the vertical-position lock is in the unlocked position. The vertical-position lock may be movable in about 4.5 degree increments.

In some embodiments, each movable pin included in the set of movable pins may be spaced-apart circumferentially an equal distance from each neighboring movable pin. Each stationary-disk hole may be spaced-apart circumferentially an equal distance from each neighboring stationary-disk hole. Each movable-disk hole may be spaced-apart circumferentially an equal distance from each neighboring movable-disk hole.

According to another aspect of the present disclosure, a limb holder includes a joint, a spar, and a multi-axis joint. The joint mount is adapted to couple to a support platform in a fixed position. The spar extends in an outward direction away from the joint mount and is adapted to couple to a patient's limb. The multi-axis joint includes a vertical-position lock and a horizontal-position lock. The horizontal-position lock interconnects the spar and the vertical-position lock and is movable between a blocking position in which movement of the spar and the vertical-position lock is blocked and an unblocking position in which the spar and the vertical-position lock are freed to move together relative to the joint mount about a horizontal axis. The vertical-position lock interconnects the spar and the horizontal-position lock and is movable between a locked position in which the spar is blocked from moving relative to the horizontal-position lock and the joint mount and an unlocked position in which the spar is freed to move relative to the horizontal-position lock and the joint mount. The patient's limb may be retained in traction throughout movement of the spar relative to the joint mount.

Additional features, which alone or in combination with any other feature(s), including those listed above, those listed in the claims, and those described in detail below, may comprise patentable subject matter. Other features will become apparent to those skilled in the art upon consideration of the following detailed description of illustrative embodiments exemplifying the best mode of carrying out the invention as presently perceived.

BRIEF DESCRIPTIONS OF THE DRAWINGS

The detailed description particularly refers to the accompanying figures in which:

FIG. 5 is an enlarged partial perspective view of the two-axis leg holder of FIGS. 1-4 showing a horizontal-lock actuator in an engaged position causing a horizontal-position lock to remain in the blocking position blocking movement of the two-axis leg holder about a horizontal axis relative to the support platform;

FIG. 6 is a sectional view taken along line 6-6 of FIG. 5 showing the horizontal-position lock in the blocking position;

FIG. 7 is a view similar to FIG. 5 showing the horizontal-lock actuator in an engaged position causing the horizontal-position lock to move to the unblocking position as suggested in FIG. 8;

FIG. 8 is a sectional view taken along line 8-8 of FIG. 7 showing the horizontal-position lock moved to the unblocking position;

FIG. 9 is a view similar to FIG. 5 showing a vertical-lock actuator in a disengaged position causing a vertical-position lock to remain in a locked position blocking movement of the two-axis leg holder about a vertical axis relative to the support platform;

FIG. 10 is a sectional view taken along line 10-10 of FIG. 9 showing the vertical-position lock in the locked position;

FIG. 11 is a view similar to FIG. 9 showing the vertical-position lock moved to the unlocked position allowing movement of the movable leg support relative to the support platform;

FIG. 12 is a sectional view taken along line 12-12 of FIG. 11 showing the vertical-position lock moved to the unlocked position;

FIG. 15 is an enlarged partial perspective view of the two-axis leg holder of FIGS. 13 and 14 showing a horizontal-lock actuator in a disengaged position causing a horizontal-position lock included in the two-axis leg holder to remain in the blocking position blocking movement of the two-axis leg holder about a horizontal axis relative to the support platform;

FIG. 16 is a sectional view taken along line 16-16 of FIG. 15 showing the horizontal-position lock in the blocking position;

FIG. 17 is a view similar to FIG. 15 showing the horizontal-lock actuator in an engaged position causing the horizontal-position lock to move to the unblocking position as suggested in FIG. 18;

FIG. 18 is a sectional view taken along line 18-18 of FIG. 17 showing the horizontal-position lock moved to the unblocking position;

DETAILED DESCRIPTION

Figure 1:
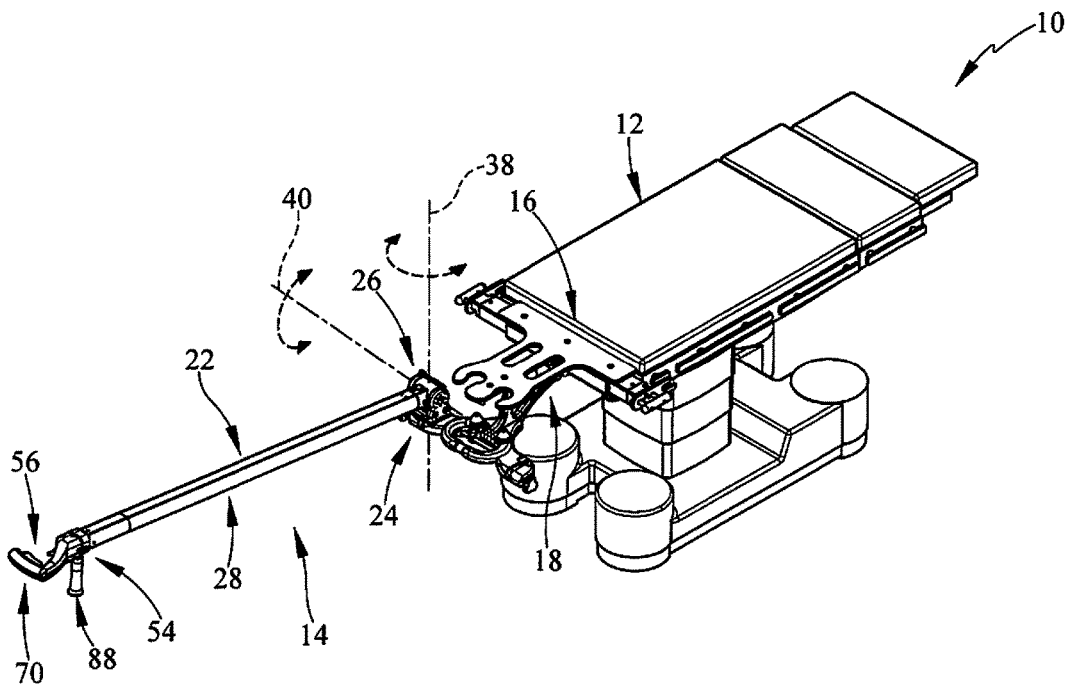
FIG. 1 is a perspective view of a support apparatus in accordance with the present disclosure showing that the support apparatus includes a surgical table and one embodiment of a limb-support unit coupled to a foot end of the surgical table.
Figure 2:
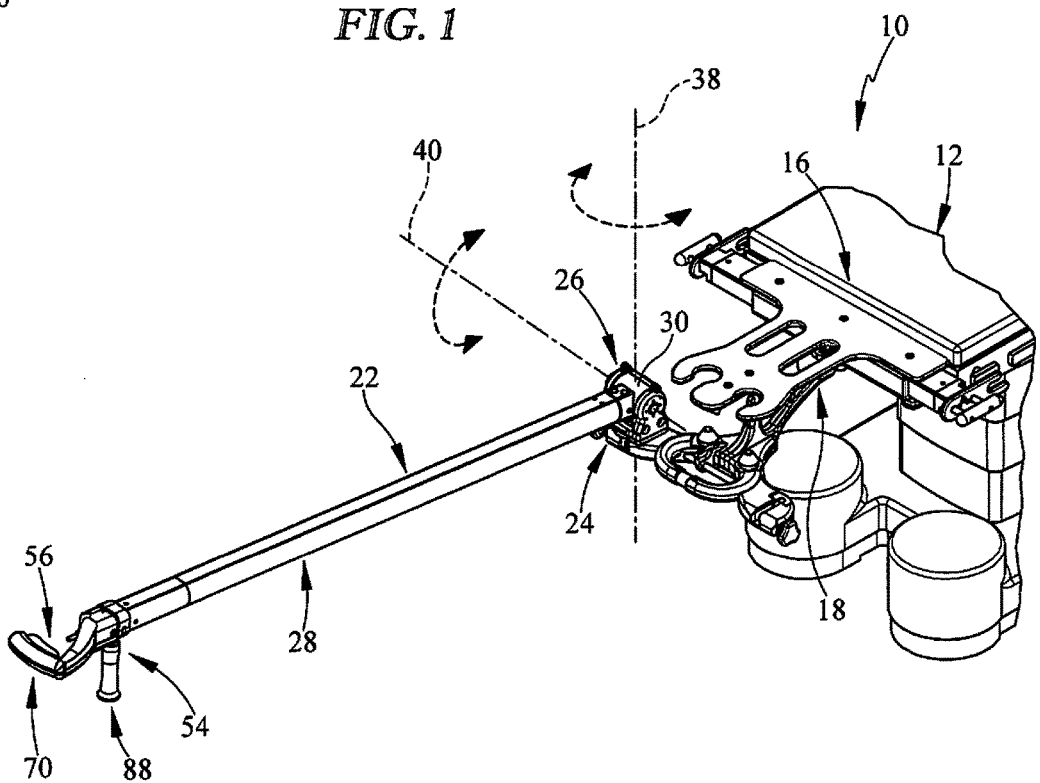
FIG. 2 is an enlarged partial perspective view of the limb-support unit of FIG. 1.
Figure 3:
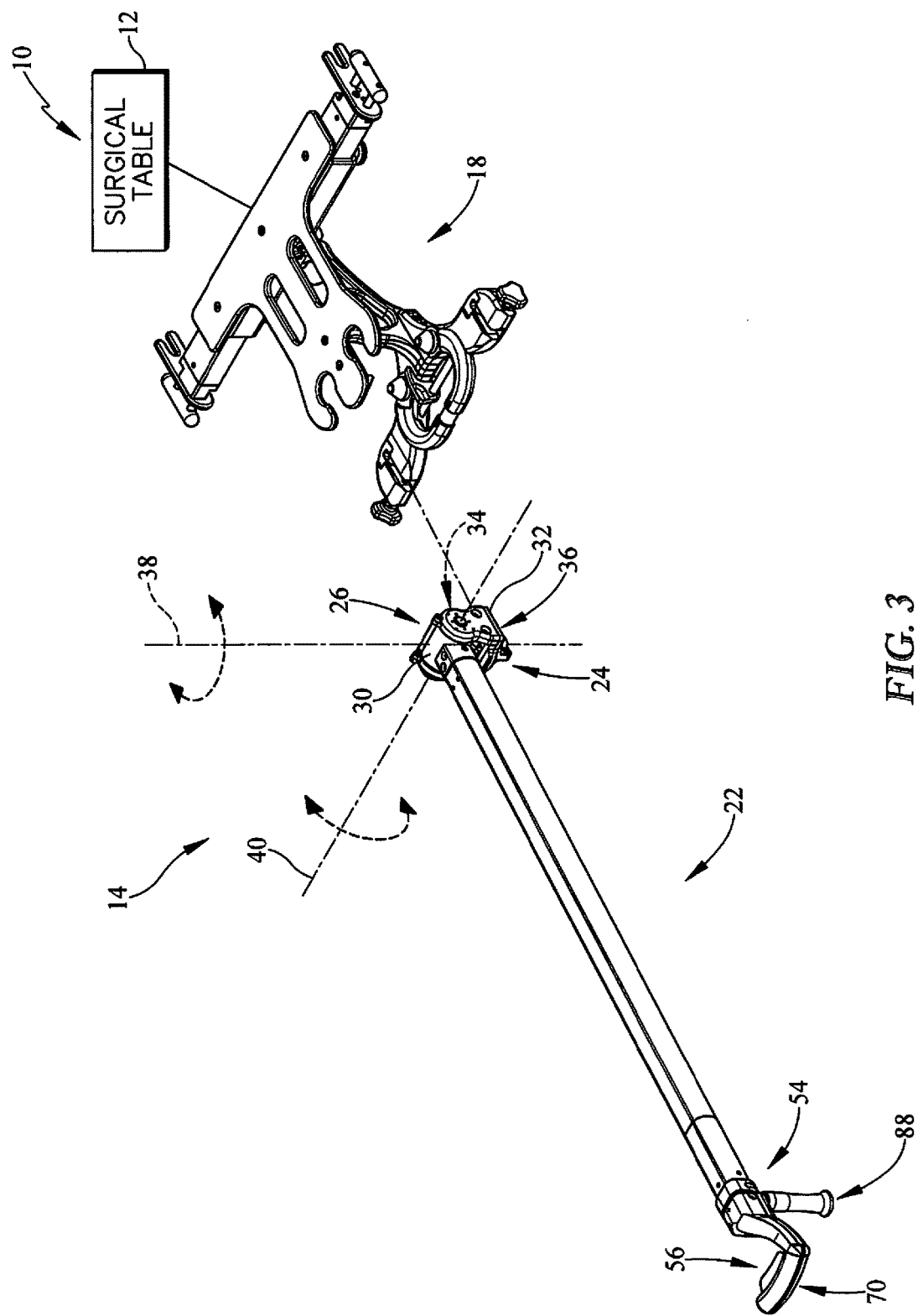
FIG. 3 is an exploded assembly view of the limb-support unit of FIG. 1 showing that the limb-support unit includes a two-axis leg holder and a support platform.

A support apparatus 10 includes, for example, a surgical table 12 and a limb-support unit 14 as shown in FIGS. 1-3. The limb-support unit 14, for example, is coupled to a foot end 16 of the surgical table 12 as shown in FIGS. 1 and 2. In an example of use, the limb-support unit 14 supports a patient's legs (not shown) and the surgical table 12 supports a patient's upper body (not shown). The limb-support unit 14 may be used to place tension on the patient's legs during surgery. This is also called placing the patient's legs in traction. During a hip surgery, the patient's leg being operated on may need to be repositioned to provide the surgeon with improved access while maintaining the patient's leg in traction. The limb-support unit 14, in accordance with the present disclosure, provides the ability to reposition the patient's leg while maintaining that leg in traction. However, the limb-support unit 14 may be used to support a patient's arm (not shown) in tension as well.

The limb-support unit 14 includes a support platform 18, also called platform 18, and a two-axis limb holder 22, also called a two-axis leg holder 22, as shown in FIGS. 1-3. The support platform 18 is coupled to the foot end 16 of the surgical table 12 in a fixed position as shown in FIGS. 1 and 2. The limb-support unit 14 may also include a one-axis leg holder that is coupled to the support platform 18 in a fixed position when supporting one of the patient's legs. When the one-axis leg holder is not supporting one of the patient's legs, the one-axis leg holder may be repositioned relative to the support platform 18. The two-axis leg holder 22 is coupled to the support platform 18 as shown in FIGS. 1 and 2. Portions of the two-axis leg holder 22 move relative to the support platform 18 as suggested in FIGS. 1 and 2.

Figure 4:
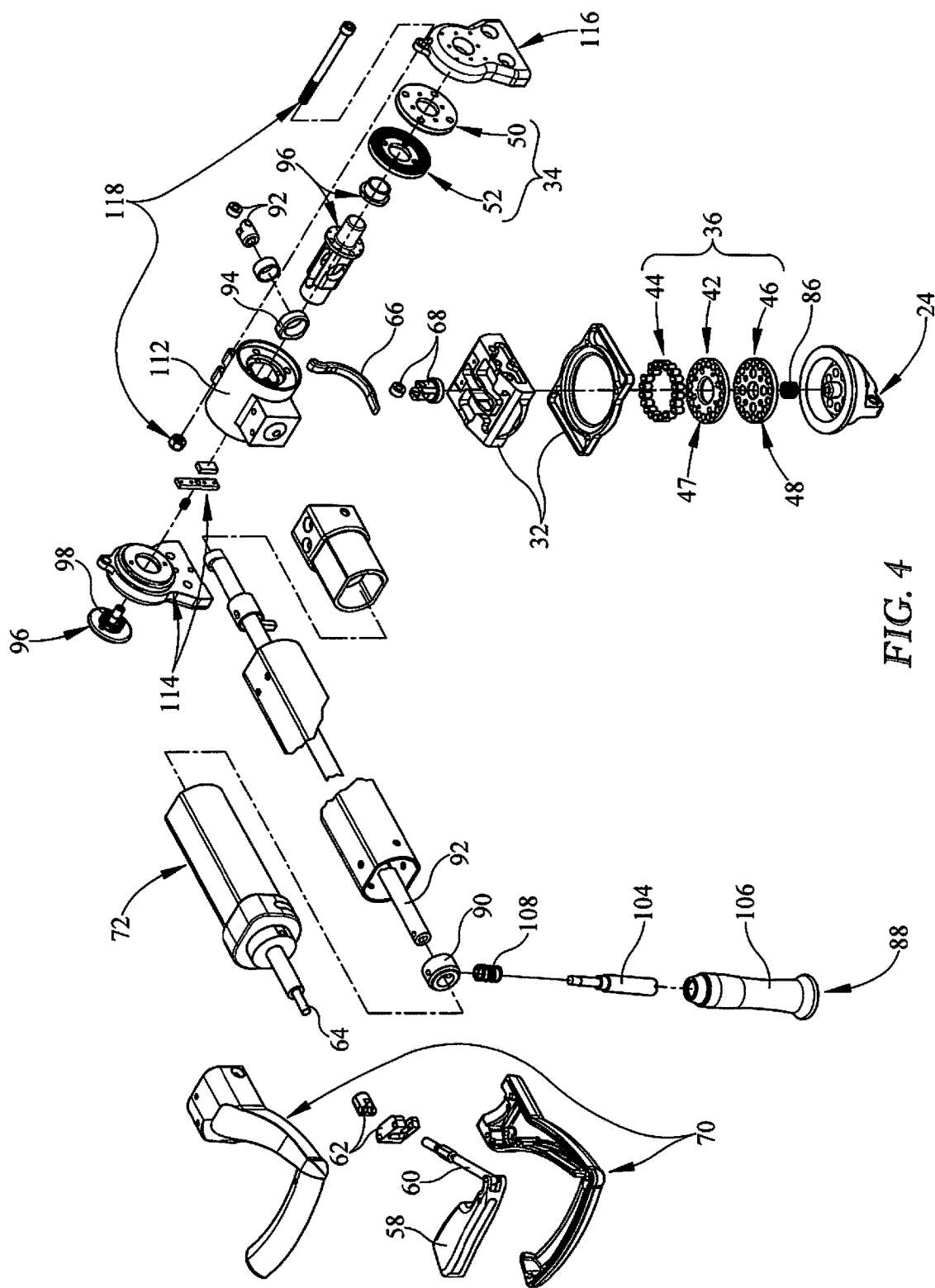
FIG. 4 is an exploded assembly view of the two-axis leg holder of FIG. 3.

The two-axis leg holder 22 includes a joint mount 24, a multi-axis joint 26, and a spar 28 as shown in FIGS. 3 and 4. The joint mount 24 is coupled to the support platform 18 in a fixed position while the limb-support unit 14 supports portions of the patient. When the limb-support unit 14 is not supporting portions of the patient, the joint mount 24 may be decoupled from the support platform 18 and repositioned on the support platform 18. The multi-axis joint 26 is arranged to interconnect the spar 28 and the joint mount 24 to cause the spar 28 to move relative to the joint mount 24 as suggested in FIG. 4. The spar 28 is coupled to the multi-axis joint 26 and arranged to extend away from the multi-axis joint 26 to support the patient's leg in traction during surgery.

The multi-axis joint 26 includes a joint housing 30, a support platform 32, a vertical-position lock 34, and a horizontal-position lock 36 as shown in FIGS. 4-12. The horizontal-position lock 36 lies between and interconnects the joint mount 24 and the support platform 32. The joint housing 30 is coupled to the support platform 32 to move with the support platform 32. The vertical-position lock 34 interconnects portions of the joint housing 30 and the spar 28. Together, the vertical-position lock 34 and the horizontal-position lock 36 cooperate to control movement of the spar 28 relative to the joint mount 24 as suggested in FIGS. 1-3.

The horizontal-position lock 36 is movable between a blocking position shown in FIGS. 5 and 6 and an unblocking position shown in FIGS. 7 and 8. The horizontal-position lock 36, when in the blocking position, blocks movement of the spar 28, the vertical-position lock 34, the joint housing 30, and the support platform 32 relative to the joint mount 24. When the horizontal-position lock 36 is in the unblocking position, the spar 28, the vertical-position lock 34, the joint housing 30, and the support platform 32 are freed to rotate together as a unit about a vertical axis 38 relative to the joint mount 24.

The vertical-position lock 34 is movable between a locked position shown in FIGS. 9 and 10 and an unlocked position shown in FIGS. 11 and 12. When the vertical-position lock 34 is in the locked position, the vertical-position lock 34 blocks movement of the spar 28 relative to portions of the joint housing 30, the horizontal-position lock 36, and the support platform 32. When the vertical-position lock 34 is in the unlocked position, the vertical-position lock 34 allows the spar 28 to move about a horizontal axis 40. The vertical-position lock 34 may move between the locked and the unlocked positions when the horizontal-position lock 36 is in either the blocking or the unblocking positions. The horizontal-position lock 36 may move between the blocking and the unblocking position when the vertical-position lock 34 is in either the locked or the unlocked position.

The horizontal-position lock 36 includes a stationary disk 42, a set 44 of movable pins, and a movable disk 46 as shown in FIG. 4. As an example, the set 44 of movable pins includes twenty pins spaced-apart radially from one another an equal amount. Stationary disk 42 is coupled to the support platform 32 in a fixed position relative to the support platform 32. The set 44 of movable pins are trapped between the stationary disk 42 and the support platform 32 and spring biased to extend away from the support platform 32. The set 44 of pins are configured to move through an associated set 47 of holes formed in the stationary disk between a retracted position and an extended position. The set 47 of holes includes twenty holes aligned with the set 44 of twenty pins. The movable disk 46 is coupled to the joint mount 24 to move relative to the joint mount 24, the stationary disk 42, and the set 44 of pins.

When the horizontal-position lock 36 is in the blocking position, the movable disk 46 lies in confronting relation with the stationary disk 42 and four pins of the set 44 of pins extend through four holes of the set 47 of holes in the stationary disk 42 and extend into four holes formed in the movable disk 46. The movable disk 46 is formed to include a set 48 of sixteen holes therein. The sixteen holes are spaced-apart radially from one another an equal amount. When the horizontal-position lock is in the unblocking position, the movable disk 46 is spaced apart from the stationary disk 42 a distance sufficient to cause the four pins to be withdrawn from the four holes formed in the movable disk 46 allowing the stationary disk 42 to rotate about the vertical axis 38 with the support platform 32 relative to the movable disk 46.

Because the stationary disk 42 includes twenty holes, there are twenty pins, and the movable disk 46 includes sixteen holes, only four holes in the stationary disk 42, four pins, and four holes in the movable disk 46 align every about 4.5 degrees. As a result, the horizontal-position lock can be adjusted in about 4.5 degree increments. However, the number holes in the stationary disk 42, the number of pin in set 44, and the number of holes in movable disk 46 may be changed to suit the increment desired.

The vertical-position lock 34, also called a hirth joint or hirth coupling, includes a stationary plate 50 and a movable plate 52 as shown in FIG. 4. The stationary plate 50 is coupled to a second shell support 116 included in joint housing 30 to move with the second shell support 116. The movable plate 52 is coupled to a housing shell 112 included in the joint housing 30 to move back and forth with the housing shell 112 along the horizontal axis 40 relative to the stationary plate 50. When the vertical-position lock 34 is in the locked position, the movable plate 52 lies in confronting engaging relation with stationary plate 50 as shown in FIG. 10. When the vertical-position lock 34 is in the unlocked position, the movable plate 52 is spaced apart from the stationary plate 50 allowing the movable plate 52 to rotate up and down about horizontal axis 40 relative to shell supports 114, 116 and stationary plate 50.

As an example, the stationary plate 50 includes a disk and a plurality of radially-extending inwardly-projecting teeth appended to the disk. The plurality of radially-extending inwardly-projecting teeth extend towards the movable plate 52. The movable plate 52 includes a disk and a plurality of radially-extending outwardly-projecting teeth appended to the disk. The radially-extending outwardly-projecting teeth extend toward the stationary plate 50. The teeth appended to both disk are numbered so as to compliment one another and are configured to mate with one another when the vertical-position lock 34 is in the locked position. The vertical-position lock 34 allows for adjustments in position of the spar 28 in about 4 degree increments. However, the design of the stationary plate 40 and the movable plate 52 may be varied to achieve the increment desired.

Each of the vertical-position lock 34 and the horizontal-position lock 36 are movable independently of one another as suggested in FIGS. 1 and 2. Vertical-position lock 34 is moved by a vertical-lock actuator 54 included in the two-axis leg holder 22 as shown in FIGS. 9-12. The horizontal-position lock 36 is moved by the horizontal-lock actuator 56 included in the two-axis leg holder 22 as shown in FIGS. 5-8. The vertical-lock actuator 54 is coupled to the spar 28 and to the vertical-position lock 34 and is movable to cause the vertical-position lock 34 to move between the locked and unlocked positions. The horizontal-lock actuator 56 is coupled to the spar 28 and to the horizontal-position lock 36 and is movable to cause the horizontal-position lock 36 to move between the blocking and the unblocking positions.

The horizontal-lock actuator 56 includes a trigger 58, a first trigger linkage 60, a second trigger linkage 62, a connecting linkage 64, a lever 66, and a drive linkage 68 as shown in FIGS. 4 and 5-8. The trigger 58 is coupled to a spar handle 70 included in the spar 28 to move relative to the spar handle 70 in response to application of an actuation force F to the trigger 58. The first trigger linkage 60 interconnects the trigger 58 and the second trigger linkage 62 as shown in FIGS. 5 and 7. The second trigger linkage 62 interconnects the first trigger linkage 60 and the connecting linkage 64 which extends along a beam 72 included in the spar 28. The connecting linkage 64 is coupled to the lever 66 to cause the lever to pivot about a lever axis 74 as shown in FIGS. 6 and 8. The lever is configured to engage and move the drive linkage 68 which is coupled to the movable disk 46 included in the vertical-position lock 34.

In an example of use, a caregiver applies the actuation force F to the trigger 58 causing the trigger 58 to pivot in a counter-clockwise direction 76 about a first trigger axis 78 as suggested in FIG. 5 and shown in FIG. 7. Movement of the trigger 58 causes the first trigger linkage 60 to move toward the beam 72 which causes the second trigger linkage 62 to rotate about a second trigger axis 80 in the counter-clockwise direction 76. Movement of the second trigger linkage 62 causes the connecting linkage 64 to be driven toward the multi-axis joint 26 as suggested in FIGS. 5 and 6 and shown in FIGS. 7 and 8. Movement of the connecting linkage 64 causes the lever 66 to be rotated about the lever axis 74 in a counter-clockwise direction 82. Rotation of the lever 66 engages and moves the drive linkage 68 in a downward direction 84 as suggested in FIG. 6 and shown in FIG. 8. The movable disk 46 is coupled to the drive linkage 68 to move therewith and moves downwardly out of engagement with the pins included in the set 44 of pins. As a result, the horizontal-position lock 36 is moved to the unlocked position freeing the vertical-position lock 34, portions of the joint housing 30, and the spar 28 to move about the vertical axis 38 relative to the joint mount 24.

The horizontal-lock actuator 56 further includes a horizontal-lock bias spring 86 which provides a bias force to urge the horizontal-position lock 36 to return to the blocking position when the actuation force F is removed. The horizontal-lock bias spring 86 is positioned to lie between the joint mount 24 and the drive linkage 68 as shown in FIGS. 4, 6, and 8.

The vertical-lock actuator 54 includes a grip 88, a rotation collar 90, a rotation linkage 92, a cam 94, a cam follower 96, and a bias mechanism 98 as shown in FIG. 4 and suggested in FIGS. 9-12. The grip 88 is coupled to the spar handle 70 to extend perpendicularly away from the spar handle 70 as shown in FIGS. 9 and 11. The rotation collar 90 is coupled to the grip 88 to move therewith as the grip 88 is rotated about a rotation axis 100 in a counter-clockwise direction 110 as suggested in FIG. 9 and shown in FIG. 11. The rotation axis 100 is defined by the rotation linkage 92. The rotation collar 90 is also coupled to the spar handle 70 to rotate relative to the spar handle 70. The rotation linkage 92 interconnects the rotation collar 90 and the cam 94 to cause movement of the rotation collar 90 to be translated to the cam 94. The rotation linkage is arranged to extend between the multi-axis joint 26 and the spar handle 70. The rotation linkage 92 is formed to include a hollow passageway therein and the connecting linkage 64 of the horizontal-lock actuator 56 is configured to extend there through for movement independent of the rotation linkage 92. The cam follower 96 is coupled to the movable plate 52 and the housing shell 112 to cause the movable plate 52, the cam follower 96, and the housing shell 112 to move back and forth along the horizontal axis 40 in response to movement of the cam 94.

The bias mechanism 98 is positioned to lie between a portion of the cam follower 96 and a first shell support 114 included in joint housing 30 to cause the cam follower 96 and the movable plate 52 to move away from the stationary plate 50 as shown in FIGS. 9 and 11. The bias mechanism 98 provides another bias force to urge the vertical-position lock 34 to the unlocked position when the rotation force R is removed from the grip 88.

The spar 28 is capable of moving about the horizontal axis 40 through a range of motion of about 20 degrees down from a generally horizontal position and about 55 degrees up from a generally horizontal position. The two-axis leg holder 22 is also configured to support a portion of a 350 pound patient with an inseam of about 42 inches. As a result, the two-axis leg holder 22 can withstand a torque of about 250 foot pounds when the spar 28 is generally horizontal.

The grip 88 of vertical-lock actuator 54 includes a rod 104, a grip shell 106, and a shell bias spring 108 as shown in FIG. 4. The rod 104 is coupled to the rotation collar 90 to move therewith. The grip shell 106 is coupled to the rod 104 to move back and forth relative to the rod 104 between a first position and a second position. The shell bias spring 108 is coupled to the rod and the grip shell 106 to bias the grip shell 106 into the first position. When the grip shell 106 is in the first position, an upper tapered portion of the grip shell 106 is arranged to mate with an associated tapered portion formed in the beam 72. The two tapered portions cooperate to maintain grip shell 106 in the first position. When the grip shell 106 is in the second position, the grip shell 106 is spaced apart from the beam 72 such that the two tapered portions are no longer engaged with one another. As a result, grip 88 is freed to rotate about the rotation axis 100 when in the second position.

As shown in FIG. 4, the joint housing 30 includes a housing shell 112, a first shell support 114, a second shell support 116, and a shell coupler 118. The housing shell 112 is positioned to lie between and interconnect the first and the second shell supports 114, 116. The housing shell 112 is coupled to the support platform 32 to extend upwardly away from the support platform 32. The first and second shell supports 114, 116 are coupled to the support platform 32 and configured to receive portions of the cam follower 96 therein and provide rotative bearing engagement between the cam follower 96 and the shell supports 114, 116. The shell coupler 118 is coupled to both the shell supports 114, 116 and is configured to maintain the shell supports 114, 116 in spaced-apart relation to one another trapping the housing shell 112 therebetween. As an example, the shell coupler 118 is a nut and a bolt.

Figure 13:
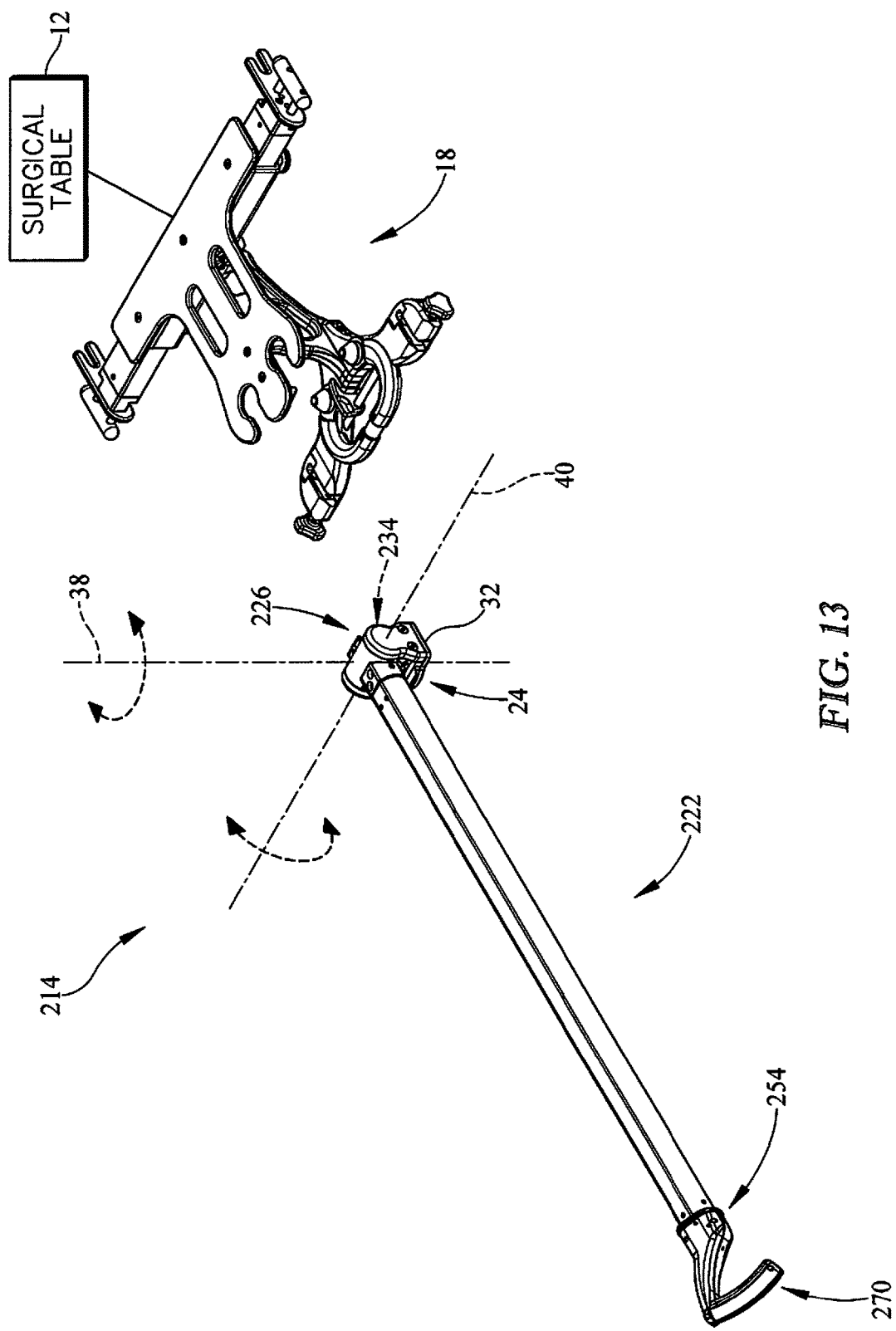
FIG. 13 is an exploded assembly view of a limb-support unit showing that the limb-support unit includes another embodiment of a two-axis leg holder in accordance with the present disclosure.
Figure 14:
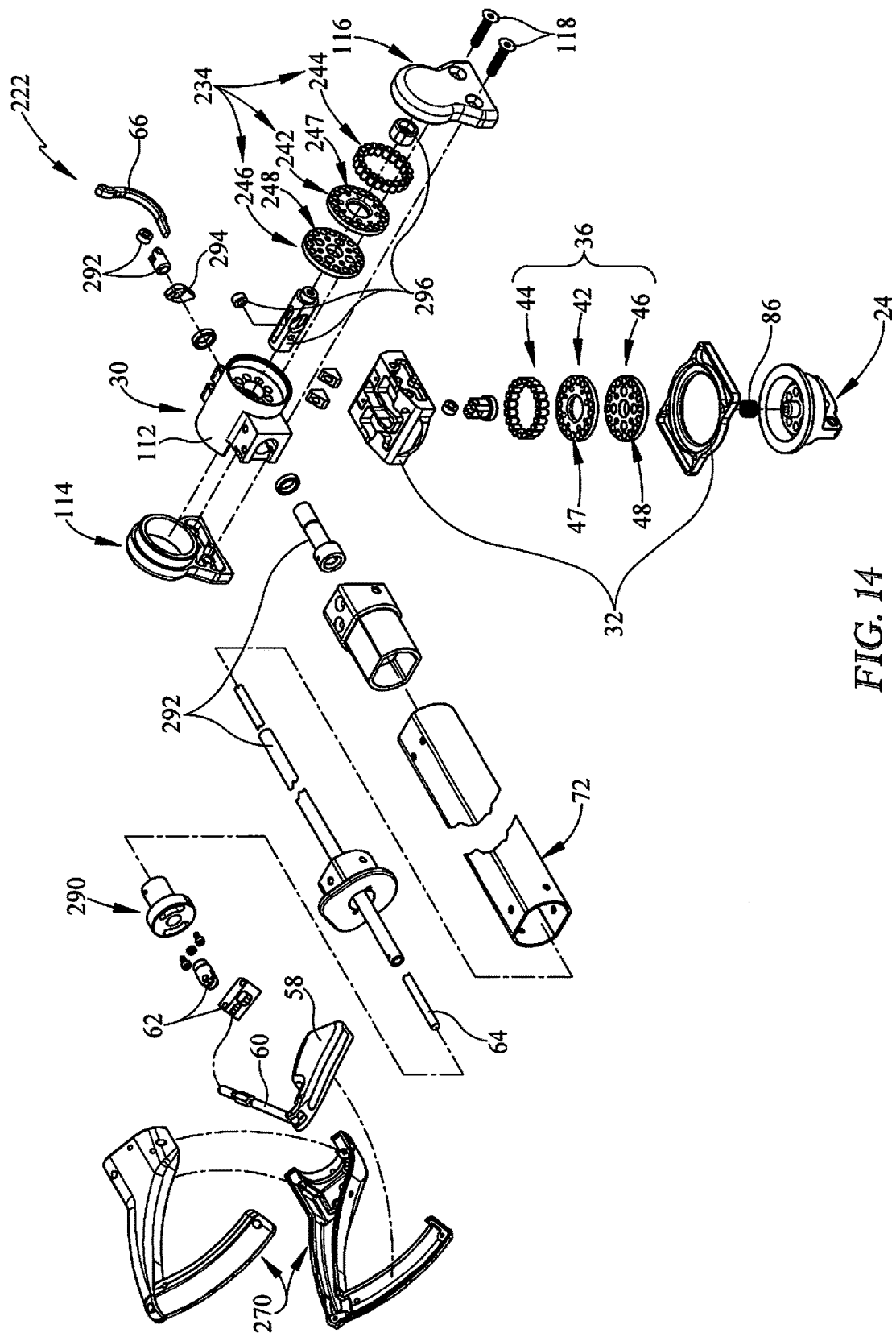
FIG. 14 is an exploded assembly view of the two-axis leg holder of FIG. 13.

Another embodiment of a limb-support unit 214 includes the support platform 18 and a two-axis leg holder 222 as shown in FIG. 13. The two-axis leg holder 222 includes the joint mount 24, a multi-axis joint 226, and a spar 28 as shown in FIGS. 13 and 14. The multi-axis joint 226 is arranged to interconnect the spar 28 and the joint mount 24 to cause the spar 28 to move relative to the joint mount 24 as suggested in FIG. 4. The spar 28 is coupled to the multi-axis joint 226 and arranged to extend away from the multi-axis joint 226 to support the patient's leg in traction during surgery.

The multi-axis joint 226 includes the joint housing 30, the support platform 32, a vertical-position lock 234, and the horizontal-position lock 36 as shown in FIGS. 14-22. The horizontal-position lock 36 lies between and interconnects the joint mount 24 and the support platform 32. The joint housing 30 is coupled to the support platform 32 to move with the support platform 32. The vertical-position lock 234 interconnects the joint housing 30 and the spar 28. Together, the vertical-position lock 234 and the horizontal-position lock 36 cooperate to control movement of the spar 28 relative to the joint mount 24 as suggested in FIG. 13.

The horizontal-position lock 36 is movable between a blocking position shown in FIGS. 15 and 16 and an unblocking position shown in FIGS. 17 and 18. The horizontal-position lock 36, when in the blocking position, blocks movement of the spar 28, the vertical-position lock 234, the joint housing 30, and the support platform 32 relative to the joint mount 24. When the horizontal-position lock 36 is in the unblocking position, the spar 28, the vertical-position lock 234, the joint housing 30, and the support platform are freed to rotate together as a unit about the vertical axis 38 relative to the joint mount 24.

Figures 19, 20:
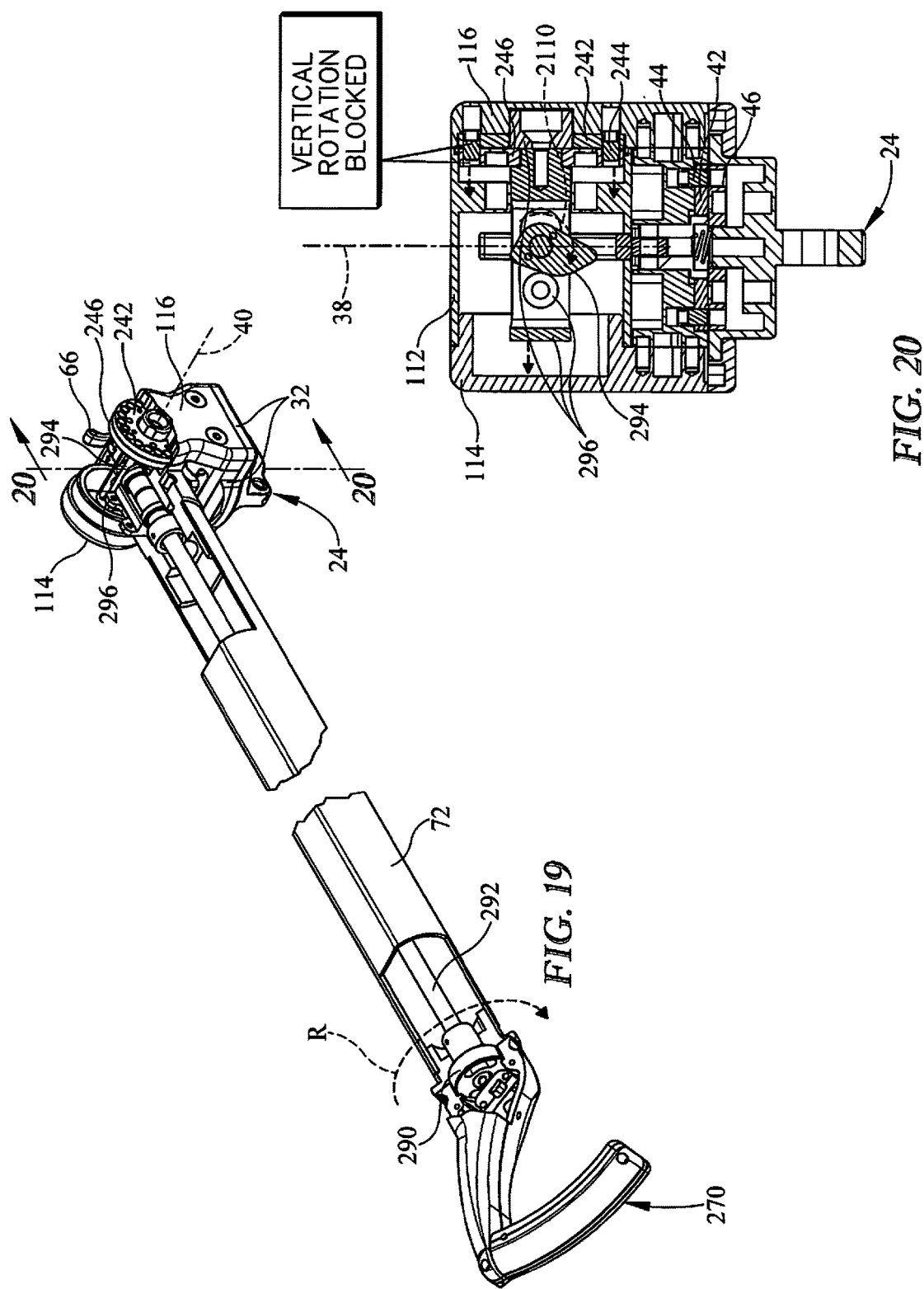
FIG. 19 is a view similar to FIG. 15 showing a vertical-lock actuator in a disengaged position causing a vertical-position lock to remain in a locked position.
FIG. 20 is a sectional view taken along line 20-20 of FIG. 19 showing the vertical-position lock in the locked position.
Figures 21, 22:
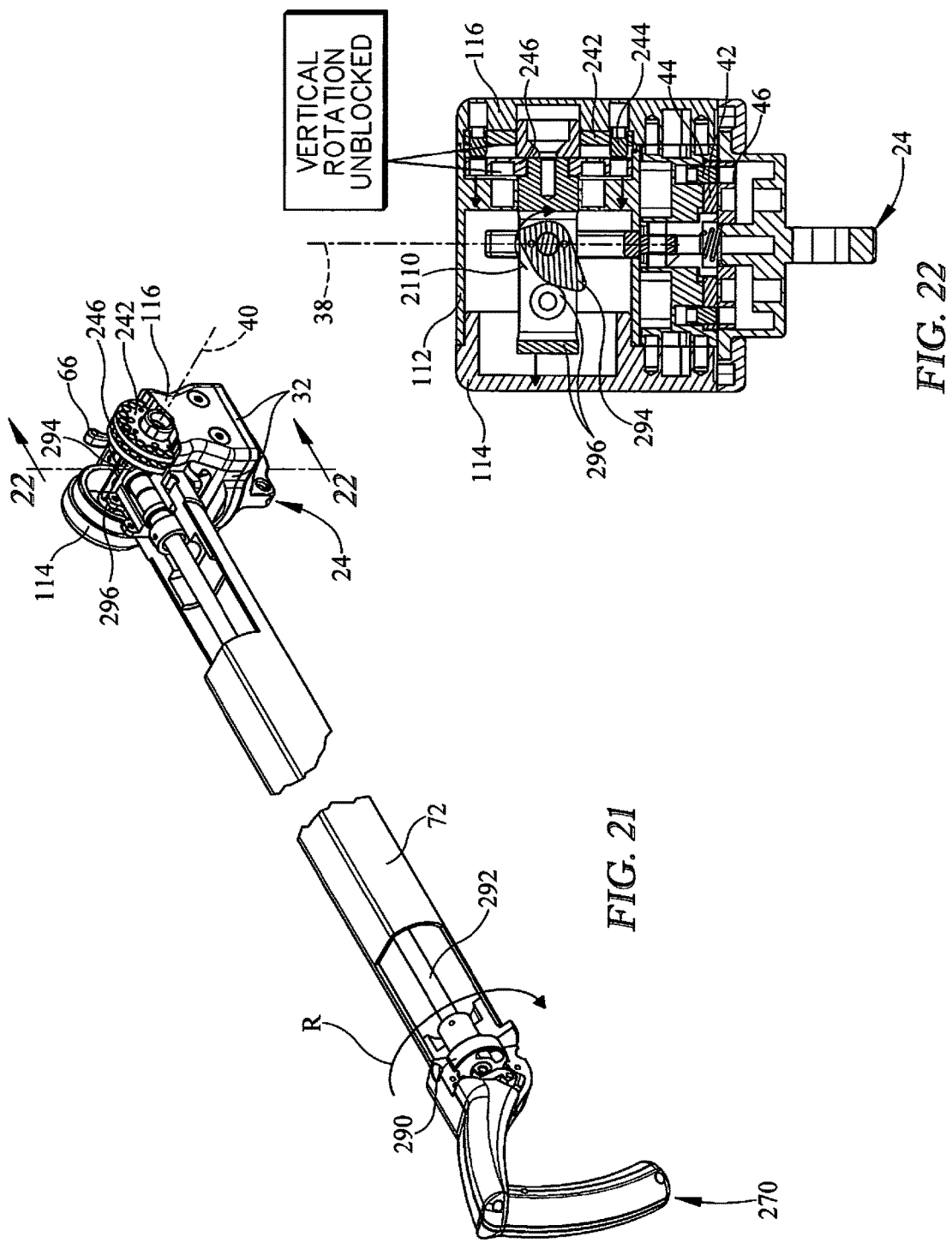
FIG. 21 is a view similar to FIG. 19 showing the vertical-position lock moved to the unlocked position.
FIG. 22 is a sectional view taken along line 22-22 of FIG. 21 showing the vertical-position lock moved to the unlocked position.

The vertical-position lock 234 is movable between a locked position shown in FIGS. 19 and 20 and an unlocked position shown in FIGS. 21 and 22. When the vertical-position lock 234 is in the locked position, the vertical-position lock 234 blocks movement of the spar 28 relative to the joint housing 30, the horizontal-position lock 36, and the support platform 32. When the vertical-position lock 234 is in the unlocked position, the vertical-position lock 234 allows the spar 28 to move about the horizontal axis 40. The vertical-position lock 234 may move between the locked and the unlocked positions when the horizontal-position lock 36 is in either the blocking or the unblocking positions. The horizontal-position lock 36 may move between the blocking and the unblocking position when the vertical-position lock 234 is in either the locked or the unlocked position.

The vertical-position lock 234 includes a vertical stationary disk 242, a set 244 of movable pins, and a vertical movable disk 246 as shown in FIG. 14. As an example, the set 244 of movable pins includes twenty pins spaced-apart radially from one another an equal amount. Vertical stationary disk 242 is coupled to the joint housing 30 in a fixed position relative to the joint housing 30. The set 244 of movable pins are trapped between the vertical stationary disk 242 and the joint housing 30. The set 244 of pins are configured to move through an associated set 247 of holes formed in the vertical stationary disk 242 between a retracted position and an extended position. The set 247 of holes includes twenty holes aligned with the set 244 of twenty pins. The vertical movable disk 246 is coupled to the joint housing 30 to move relative to the joint housing 30, the vertical stationary disk 242, and the set 244 of pins.

When the vertical-position lock 234 is in the locked position, the vertical movable disk 246 lies in confronting relation with the vertical stationary disk 242 and four pins of the set 244 of pins extend through four holes of the set of holes in the vertical stationary disk 242 and extend into four holes formed in the vertical movable disk 246. The vertical movable disk 246 is formed to include a set 248 of holes therein. As an example, the set 248 of holes includes sixteen holes spaced-apart radially from one another an equal amount. When the vertical-position lock 234 is in the unlocked position, the vertical movable disk 246 is spaced apart from the vertical stationary disk 242 to cause the four pins to be withdrawn from the four holes formed in the vertical movable disk 246 allowing the vertical stationary disk 242 to rotate about the horizontal axis 40 with the spar 28.

Because the vertical stationary disk 242 includes twenty holes, there are twenty pins, and the vertical movable disk 246 includes sixteen holes, only four holes in the vertical stationary disk 242, four pins, and four holes in the vertical movable disk 246 align every 4.5 degrees. As a result, the vertical-position lock 234 can be adjusted in 4.5 degree increments. However, the number holes in the vertical stationary disk 242, the number of pins in the set 244, and the number of holes in the vertical movable disk 246 may be changed to suit the increment desired.

Each of the vertical-position lock 234 and the horizontal-position lock 36 are movable independently of one another. The vertical-position lock 234 is moved by a vertical-lock actuator 254 included in two-axis leg holder 222 as shown in FIGS. 19-22. The vertical-lock actuator 254 is coupled to the spar 28 and to the vertical-position lock 234 and is movable to cause the vertical-position lock 234 to move between the locked and unlocked positions.

The vertical-lock actuator 254 includes a rotation collar 290, a rotation linkage 292, a cam 294, and a cam follower 296 as shown in FIG. 14 and suggested in FIGS. 19-22. The rotation collar 290 is coupled to the spar handle 70 to move therewith as the spar handle 70 is rotated about the rotation axis 100 in a clockwise direction 2110 as suggested in FIG. 19 and shown in FIG. 21. The rotation axis 100 is defined by the rotation linkage 292. The rotation linkage 292 interconnects the rotation collar 290 and the cam 294 to cause movement of the rotation collar 290 to be translated to the cam 294. The rotation linkage 292 is arranged to extend between the multi-axis joint 226 and the spar handle 270. The rotation linkage 292 is formed to include a hollow passageway therein and the connecting linkage 64 of the horizontal-lock actuator 56 is configured to extend there through for movement independent of the rotation linkage 292. The cam follower 296 is coupled to the vertical movable disk 246 to cause the vertical movable disk 246 and the cam follower 296 to move back and forth along the horizontal axis 40 in response to movement of the cam 294. Bias may be provided to the vertical-lock actuator 254 by gravity or inclusion of a bias mechanism. Bias may cause the cam follower 296 and the vertical movable disk 246 to move away from the vertical stationary disk 242 as shown in FIGS. 19 and 21.

The vertical-lock actuator 254 may further include a vertical-lock bias spring which provides another bias force to urge the vertical-position lock 234 to return to the locked position when the rotation force R is removed from the spar handle 70. The vertical-lock bias spring may be positioned to lie between the joint housing 30 and the cam follower to bias the vertical-position lock 234 to the locked position.

Although certain illustrative embodiments have been described in detail above, variations and modifications exist within the scope and spirit of this disclosure as described and as defined in the following claims.

The invention claimed is:

1. A limb holder comprising
a mount adapted to couple to a platform in a fixed position,
a spar extending in an outward direction away from the mount and adapted to support a patient's foot relative to the mount,
a first actuator including a trigger coupled to the spar to move relative to the spar about a first axis in response to application of a first force to the trigger to cause the spar to be freed to move about a vertical axis relative to the mount, and
a second actuator including a grip coupled to the spar to move relative to the spar and the trigger about a second axis in response to application of a second force to the grip to cause the spar to be freed to move about a horizontal axis relative to the mount,
wherein the second axis is substantially perpendicular to the first axis, and
wherein the grip is movable without movement of the trigger.

2. The limb holder of claim 1, wherein the first axis is generally perpendicular to the horizontal axis.

3. The limb holder of claim 2, wherein the first axis is generally parallel to the vertical axis when the spar is in a generally horizontal position.

4. The limb holder of claim 3, wherein the second axis is generally perpendicular to the vertical axis when the spar is in a generally horizontal position.

5. The limb holder of claim 4, wherein the second axis is generally perpendicular to the horizontal axis.

6. The limb holder of claim 1, wherein the second axis is generally perpendicular to the vertical axis when the spar is in a generally horizontal position.

7. The limb holder of claim 6, wherein the second axis is generally perpendicular to the horizontal axis.

8. The limb holder of claim 1, wherein the first actuator further includes a connecting linkage coupled to the trigger to move therewith back and forth along the second axis and arranged to extend from the trigger toward the mount.

9. The limb holder of claim 1, wherein the second actuator further includes a rotation collar coupled to the grip to move therewith about the second axis and a rotation linkage coupled to the rotation collar to move therewith and arranged to extend from the rotation collar toward the mount.

10. The limb holder of claim 9, wherein the second actuator further includes a cam coupled to the rotation linkage to rotate about the second axis therewith and a cam follower engaging the cam to cause the cam follower to move back and forth along the horizontal axis in response to application of the second force.

11. The limb holder of claim 1, wherein the first actuator further includes a connecting linkage coupled to the trigger to move therewith back and forth along the second axis, the second actuator further includes a rotation collar coupled to the grip to move therewith about the second axis and a rotation linkage coupled to the rotation collar to move therewith and arranged to extend from the rotation collar toward the mount, the rotation linkage is formed to include a hollow passageway therein, and the connecting linkage is arranged to extend through the hollow passageway to move independently of the rotation linkage.

12. The limb holder of claim 11, wherein the first axis is generally perpendicular to the horizontal axis when the spar is in a generally horizontal position.

13. The limb holder of claim 12, wherein the first axis is generally parallel to the vertical axis when the spar is in a generally horizontal position.

14. The limb holder of claim 13, wherein the second axis is generally perpendicular to the vertical axis when the spar is in a generally horizontal position.

15. The limb holder of claim 14, wherein the second axis is generally perpendicular to the horizontal axis.

16. The limb holder of claim 1, wherein the grip and the trigger are movable independent of one another relative to the spar.

17. A limb holder comprising
a mount adapted to couple to a platform in a fixed position,
a spar extending in an outward direction away from the mount and adapted to support a patient's foot relative to the mount,
a first actuator including a trigger coupled to the spar to move relative to the spar about a first axis in response to application of a first force to the trigger to cause the spar to be freed to move about a vertical axis relative to the mount, and a second actuator including a grip coupled to the spar to move relative to the spar and the first actuator about a second axis in response to application of a second force to the grip to cause the spar to be freed to move about a horizontal axis relative to the mount, wherein the second axis is substantially perpendicular to the first axis, wherein the first actuator further includes a connecting linkage coupled to the trigger to move therewith back and forth along the second axis and arranged to extend from the trigger toward the mount, and wherein the first actuator further includes a lever coupled to the connecting linkage to move therewith about a pivot axis which is generally parallel to the horizontal axis.

18. The limb holder of claim 17, wherein the first actuator further includes a drive linkage engaging the lever to cause the drive linkage to move up and down generally parallel to the vertical axis in response to application of the first force.

19. The limb holder of claim 18, wherein the first force is applied along the second axis.

20. A limb holder comprising
a mount adapted to couple to a platform in a fixed position,
a spar extending in an outward direction away from the mount and adapted to support a patient's foot relative to the mount,
a first actuator including a trigger coupled to the spar to move relative to the spar about a first axis in response to application of a first force to the trigger to cause the spar to be freed to move about a vertical axis relative to the mount, and
a second actuator including a grip coupled to the spar to move relative to the spar and the first actuator about a second axis in response to application of a second force to the grip to cause the spar to be freed to move about a horizontal axis relative to the mount, wherein the second axis is substantially perpendicular to the first axis and further comprising a multi-axis joint including a vertical-position lock and a horizontal-position lock, the horizontal-position lock interconnects the spar and the vertical-position lock and is movable between a blocking position in which movement of the spar and the vertical-position lock is blocked and an unblocking position in which the spar and the vertical-position lock are freed to move together relative to the joint mount, and the vertical-position lock interconnects the spar and the horizontal-position lock and is movable between a locked position in which the spar is blocked from moving relative to the horizontal-position lock and the mount and an unlocked position in which the spar is freed to move relative to the horizontal-position lock and the mount, wherein the multi-axis joint further includes a support platform and the horizontal-position lock lies between and interconnects the mount and the support platform to cause the support platform to move relative to the mount, and wherein the horizontal-position lock includes a stationary disk coupled to the support platform in a fixed position relative to the support platform, a set of movable pins coupled to the support platform and biased to extend away from the support platform toward the mount, and a movable disk coupled to the mount to move relative to the mount, the stationary disk, and the set of movable pins when the horizontal-position lock is in the unblocking position.

21. The limb holder of claim 20, wherein the first axis is generally perpendicular to the horizontal axis, the first axis is generally parallel to the vertical axis, the second axis is generally perpendicular to the vertical axis, and the second axis is generally perpendicular to the horizontal axis.

* * * * *